US008609673B2

(12) United States Patent
Tung

(10) Patent No.: US 8,609,673 B2
(45) Date of Patent: Dec. 17, 2013

(54) VANDETANIB DERIVATIVES

(75) Inventor: Roger Tung, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 416 days.

(21) Appl. No.: 12/864,219

(22) PCT Filed: Jan. 22, 2009

(86) PCT No.: PCT/US2009/000476
§ 371 (c)(1),
(2), (4) Date: Nov. 16, 2010

(87) PCT Pub. No.: WO2009/094210
PCT Pub. Date: Jul. 30, 2009

(65) Prior Publication Data
US 2011/0117084 A1     May 19, 2011

Related U.S. Application Data

(60) Provisional application No. 61/022,810, filed on Jan. 22, 2008, provisional application No. 61/140,847, filed on Dec. 24, 2008.

(51) Int. Cl.
| | | |
|---|---|---|
| A61K 31/517 | (2006.01) | |
| C07D 239/84 | (2006.01) | |
| A61P 35/00 | (2006.01) | |
| A61P 17/06 | (2006.01) | |
| A61P 13/12 | (2006.01) | |
| A61P 29/00 | (2006.01) | |

(52) U.S. Cl.
USPC ................ 514/266.22; 544/284

(58) Field of Classification Search
USPC ................ 544/284; 514/266.22
See application file for complete search history.

(56) References Cited

U.S. PATENT DOCUMENTS

| | | | |
|---|---|---|---|
| 6,221,335 B1 | 4/2001 | Foster | |
| 6,258,951 B1 | 7/2001 | Lohmann et al. | |
| 6,440,710 B1 | 8/2002 | Keinan et al. | |
| 6,603,008 B1 | 8/2003 | Ando et al. | |
| 7,173,038 B1 * | 2/2007 | Thomas et al. | 514/266.4 |
| 7,517,990 B2 | 4/2009 | Ito et al. | |
| 2004/0158065 A1 | 8/2004 | Barth et al. | |
| 2007/0082929 A1 | 4/2007 | Gant et al. | |
| 2007/0197695 A1 | 8/2007 | Potyen et al. | |
| 2007/0219203 A1 | 9/2007 | Bakthavatchalam et al. | |
| 2008/0103122 A1 | 5/2008 | Veltri | |
| 2010/0075916 A1 | 3/2010 | Gant et al. | |

FOREIGN PATENT DOCUMENTS

| | | |
|---|---|---|
| WO | WO-95/26325 | 10/1995 |
| WO | WO-2007/118651 | 10/2007 |

OTHER PUBLICATIONS

McLafferty, F.W., "Interpretation of Mass Spectra", W.A. Benjamin, New York, 1967, inside back cover.*
International Search Report and Written Opinion dated Mar. 18, 2009 in corresponding PCT Application No. PCT/US09/00476.
Browne, T.R., Journal of Clinical Pharmacology 38: 213-220 (1998).
Baillie, T.A., Pharmacology Rev. 33:81-132 (1981).
Gouyette, A., Biomedical and Environmental Mass Spectrometry, vol. 15, 243-247 (1988).
Cherrah, Y. et al., Biomedical and Environmental Mass Spectrometry, vol. 14, Issue 11, pp. 653-657 (1987).
Dyck, L.E. et al., Journal of Neurochemistry, vol. 46, Issue 2, pp. 399-404 (1986).
Tonn, G.R., et al., Biological Mass Spectrometry, vol. 22, Issue 11, pp. 633-642 (1993).
Haskins, N.J., Biomedical Spectrometry, vol. 9, Issue 7, pp. 269-277 (1982).
Wolen, R.L., J. Clin. Pharmacology 26: 419-424 (1986).
Pieniaszek, H.J. et al., J. Clin. Pharmacol. 39:817-825 (1999).
Honma, S. et al., Drug Metab Dispos 15(4): 551 (1987).
Foster, A.B., Adv Drug Res, 14:1-40 (1985).
Fisher, M.B. et al., Current Opinion in Drug Discovery & Development 9:101-09 (2006).
Foster, A.B., "Deuterium isotope effects in studies of drug metabolism", TIPS 524-527 (Dec. 1984).
Kushner, D.J. et al: "Pharmacological Uses and Perspectives of Heavy Water and Deuterated Compounds," Can. J. Physiol. Pharmacol 77: 79-88 (1999).
Park, B.K. et al.,"Metabolism of fluorine-containing drugs", Annu. Rev. Pharmacol. Toxicol., 41 :443-70 (2001).
Gustafson et al., "Tissue Distribution and Metabolism of the Tyrosine Kinase Inhibitor ZD6474 (Zactima) in Tumor-Bearing Nude Mice following Oral Dosing", The Journal of Pharmacology and Expermentall Therapeutics, vol. 318, No. 2, pp. 872-880, 2006.
Caprelsa® (vandetanib) Tablet for Oral Use, Highlights of Prescribing Information (Jun. 2011).

* cited by examiner

*Primary Examiner* — Susanna Moore
(74) *Attorney, Agent, or Firm* — Edwards Wildman Palmer LLP; Jeffrey D. Hsi; Mark D. Russett

(57) ABSTRACT

This invention relates to novel quinazoline derivatives of the formula:

wherein each variable is as defined herein, and their acceptable acid addition salts. The invention also provides compositions comprising a compound of this invention and the use of such compositions in methods of treating diseases and conditions beneficially treated by inhibitory activity against the VEGF receptor tyrosine kinase.

17 Claims, No Drawings

VANDETANIB DERIVATIVES

CROSS-REFERENCE TO RELATED APPLICATIONS

This application is the national stage application pursuant to 35 U.S.C. §371 of PCT application PCT/US2009/000476, filed Jan. 22, 2009, which claims the benefit of U.S. Provisional Application No. 61/022,810, filed Jan. 22, 2008 and 61/140,847, filed Dec. 24, 2008. The contents of each of these applications are incorporated herein by reference in their entirety.

This invention relates to novel quinazoline derivatives and their acceptable acid addition salts. The invention also provides compositions comprising a compound of this invention and the use of such compositions in methods of treating diseases and conditions beneficially treated by inhibitory activity against the VEGF receptor tyrosine kinase.

(4-Bromo-2-fluoro-phenyl)-[6-methoxy-7-(1-methyl-piperidin-4-ylmethoxy)-quinazolin-4-yl]-amine, also known as ZD6474 and as vandetanib, modulates VEGF receptor tyrosine kinase.

Vandetanib is currently in clinical trials for the treatment of various cancers, including non-small cell lung cancer, hepatocellular carcinoma, colorectal cancer, medullary thyroid cancer, breast cancer, brain tumors, solid tumors, other lung cancer, head and neck cancer, gliomas, neuroblastomas, Von Hippel-Lindau Syndrome and kidney tumors, fallopian tube cancer, ovarian cancer, peritoneal cavity cancer, transitional cell cancer, prostate cancer, cancer of the esophagus and gastroesophageal junction, and adenocarcinoma (see http://www.clinicaltrials.gov/ct2/results?term=vandetanib).

Despite the beneficial activities of vandetanib, there is a continuing need for new compounds to treat the aforementioned diseases and conditions.

DEFINITIONS

The terms "ameliorate" and "treat" are used interchangeably and include both therapeutic and prophylactic treatment. Both terms mean decrease, suppress, attenuate, diminish, arrest, or stabilize the development or progression of a disease (e.g., a disease or disorder delineated herein), lessen the severity of the disease or improve the symptoms associated with the disease.

"Disease" means any condition or disorder that damages or interferes with the normal function of a cell, tissue, or organ.

It will be recognized that some variation of natural isotopic abundance occurs in a synthesized compound depending upon the origin of chemical materials used in the synthesis. Thus, a preparation of vandetanib will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada E et al., Seikagaku 1994, 66:15; Ganes L Z et al., Comp Biochem Physiol Mol Integr Physiol 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

The term "isotopologue" refers to a species that differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers, or less than "X" % of other stereoisomers (wherein X is a number between 0 and 100, inclusive) are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert", "t", and "t-" each refer to tertiary. "US" refers to the United States of America.

Throughout this specification, a variable may be referred to generally (e.g., "each R") or may be referred to specifically (e.g., $R^1$, $R^2$, $R^3$, etc.). Unless otherwise indicated, when a variable is referred to generally, it is meant to include all specific embodiments of that particular variable.

Therapeutic Compounds

The present invention provides a compound of Formula A:

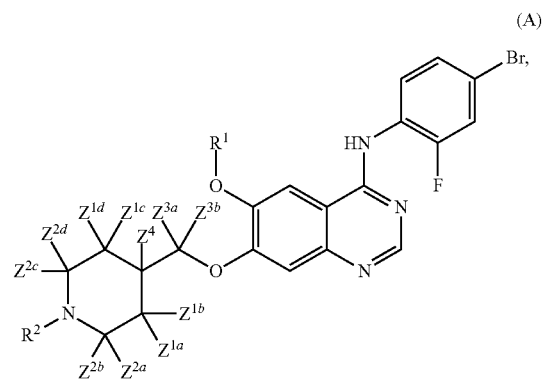

(A)

or a pharmaceutically acceptable salt thereof; wherein:
  each Z (i.e., each $Z^1$, each $Z^2$ each $Z^3$ and $Z^4$) is independently selected from hydrogen and deuterium;
  each R (i.e., $R^1$ and $R^2$) is selected from —$CH_3$, —$CH_2D$, —$CHD_2$ and $CD_3$; and
  when each R is —$CH_3$ at least one Z is deuterium.
In other embodiments of Formula A:
  a) each $Z^1$ is the same;
  b) each $Z^2$ is the same;
  c) each $Z^3$ is the same;
  d) $R^1$ is selected from $CH_3$ and $CD_3$; or
  e) $R^2$ is selected from $CH_3$ and $CD_3$.
In still other embodiments, a compound of Formula A has the features of two or more of a) through e), above.

One embodiment of a compound of Formula A is a compound of Formula I:

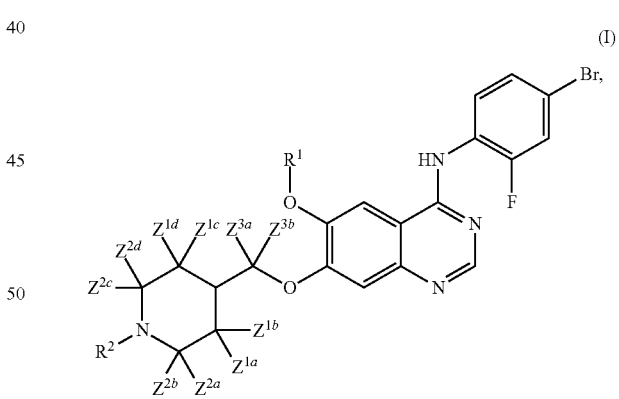

(I)

or a pharmaceutically acceptable salt thereof; wherein:
  each Z (i.e., each $Z^1$, each $Z^2$ and each $Z^3$) is independently selected from hydrogen and deuterium;
  each R (i.e., $R^1$ and $R^2$) is selected from —$CH_3$, —$CH_2D$, —$CHD_2$ and $CD_3$; and
  when each R is —$CH_3$ at least one Z is deuterium.
In other embodiments of Formula I:
  a) each $Z^1$ is the same;
  b) each $Z^2$ is the same;
  c) each $Z^3$ is the same;
  d) $R^1$ is selected from $CH_3$ and $CD_3$; or
  e) $R^2$ is selected from $CH_3$ and $CD_3$.

In still other embodiments, a compound of Formula I has the features of two or more of a) through e), above.

In yet another embodiment, the compound is selected from any one of the compounds (Cmpd) set forth in Table 1 below.

TABLE 1

Examples of Compounds of Formula I

| Cmpd | $R^1$ | $R^2$ | Each $Z^3$ | Each $Z^1$ | Each $Z^2$ |
|------|-------|-------|------------|------------|------------|
| 100 | $CD_3$ | $CH_3$ | H | H | H |
| 101 | $CH_3$ | $CD_3$ | H | H | H |
| 102 | $CH_3$ | $CH_3$ | D | H | H |
| 103 | $CD_3$ | $CH_3$ | D | H | H |
| 104 | $CH_3$ | $CD_3$ | D | H | H |
| 105 | $CD_3$ | $CD_3$ | H | H | H |
| 106 | $CD_3$ | $CD_3$ | D | H | H |
| 107 | $CD_3$ | $CH_3$ | H | D | H |
| 108 | $CH_3$ | $CD_3$ | H | D | H |
| 109 | $CH_3$ | $CH_3$ | D | D | H |
| 110 | $CD_3$ | $CH_3$ | D | D | H |
| 111 | $CH_3$ | $CD_3$ | D | D | H |
| 112 | $CD_3$ | $CD_3$ | H | D | H |
| 113 | $CD_3$ | $CD_3$ | D | D | H |
| 114 | $CD_3$ | $CH_3$ | H | H | D |
| 115 | $CH_3$ | $CD_3$ | H | H | D |
| 116 | $CH_3$ | $CH_3$ | D | H | D |
| 117 | $CD_3$ | $CH_3$ | D | H | D |
| 118 | $CH_3$ | $CD_3$ | D | H | D |
| 118 | $CD_3$ | $CD_3$ | H | H | D |
| 119 | $CD_3$ | $CD_3$ | D | H | D |
| 120 | $CD_3$ | $CH_3$ | H | D | D |
| 121 | $CH_3$ | $CD_3$ | H | D | D |
| 122 | $CH_3$ | $CH_3$ | D | D | D |
| 123 | $CD_3$ | $CH_3$ | D | D | D |
| 124 | $CH_3$ | $CD_3$ | D | D | D |
| 125 | $CD_3$ | $CD_3$ | H | D | D |
| 126 | $CD_3$ | $CD_3$ | D | D | D |

Another embodiment of a compound of Formula A is a compound of Formula Ia:

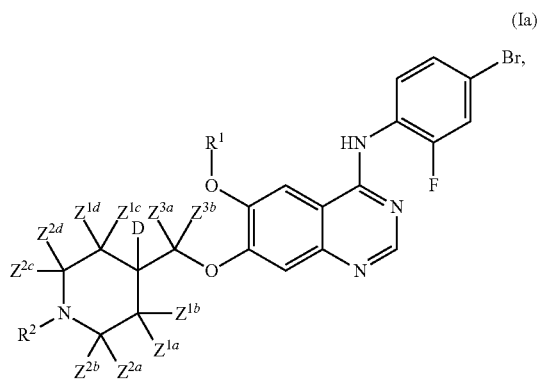

(Ia)

or a pharmaceutically acceptable salt thereof; wherein:
each Z (i.e., each $Z^1$, each $Z^2$ and each $Z^3$) is independently selected from hydrogen or deuterium; and
each R (i.e., $R^1$ and $R^2$) is selected from —$CH_3$, —$CH_2D$, —$CHD_2$ and $CD_3$.

In other embodiments of Formula Ia:
a) each $Z^1$ is the same;
b) each $Z^2$ is the same;
c) each $Z^3$ is the same;
d) $R^1$ is selected from $CH_3$ and $CD_3$; or
e) $R^2$ is selected from $CH_3$ and $CD_3$.

In still other embodiments, a compound of Formula Ia has the features of two or more of a) through e), above.

In one particular embodiment of a compound of Formula Ia, the compound is:

Compound 127

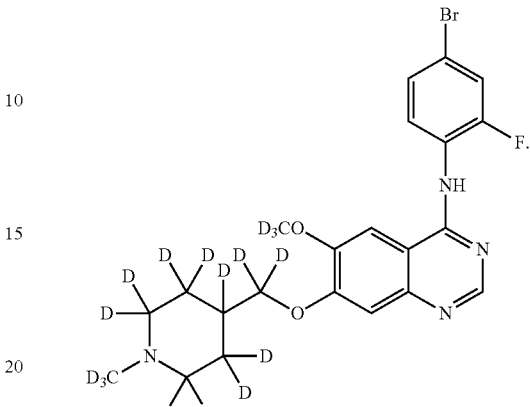

In another set of embodiments, any atom not designated as deuterium in any of the embodiments set forth above is present at its natural isotopic abundance.

The synthesis of compounds of Formula I and Ia can be readily achieved by synthetic chemists of ordinary skill. Relevant procedures and intermediates are disclosed, for instance in PCT Publications WO 00/47212, WO 01/32651, and WO 2007/036713, and in J Med Chem, 2002, 45:1300-1312.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula I is depicted in Scheme 1.

Scheme 1. Synthesis of a Compound of Formula I.

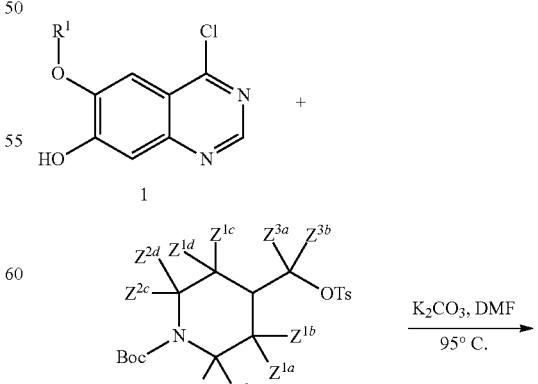

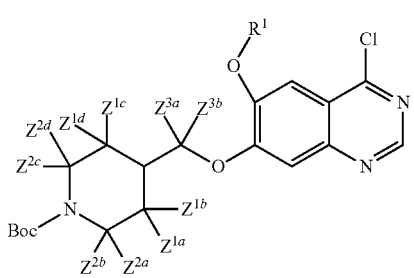

3

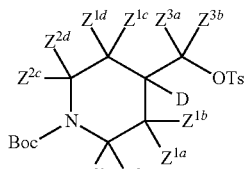

4

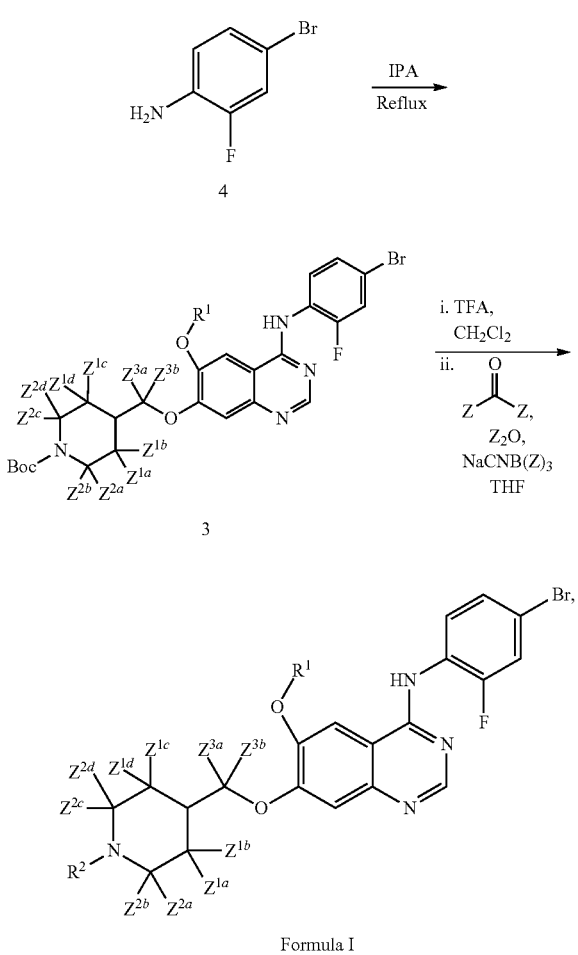

Formula I wherein each Z is independently hydrogen or deuterium.

In Scheme 1, an appropriately deuterated quinazoline 1 is combined with an appropriately deuterated and N-protected piperidinylmethyl tosylate 2 to produce 3. Intermediate 3 is then combined with commercially available 4-bromo-2-fluoro-aniline 4 in refluxing isopropyl alcohol (IPA) to produce protected intermediate 5. Intermediate 5 is then N-deprotected and subsequently N-methylated with appropriately deuterated formaldehyde, appropriately deuterated sodium cyanoborohydride and appropriately deuterated water to produce a compound of Formula I. The synthesis outlined in Scheme 1, above, can also be followed for the preparation of compounds of Formula Ia using appropriately deuterated 2a,

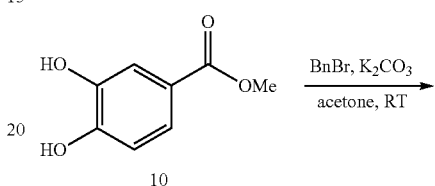

in place of reagent 2.

Scheme 2. Synthesis of Quinazoline 1.

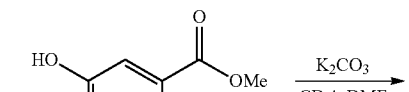

10

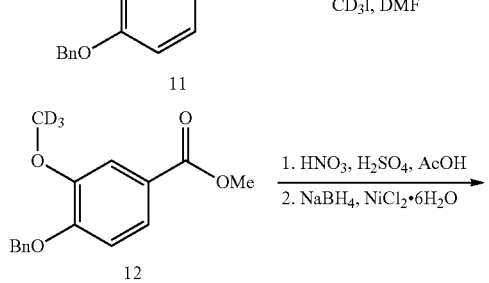

11

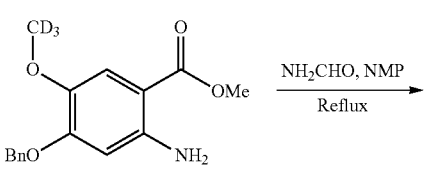

12

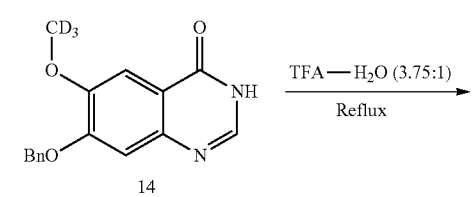

13

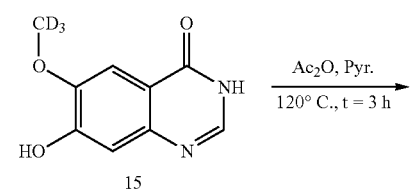

14

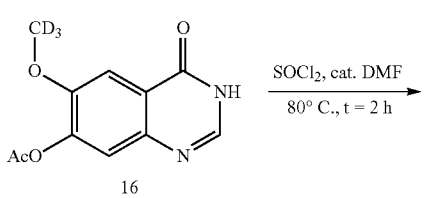

15

16

-continued

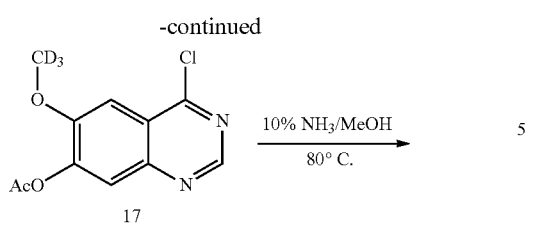

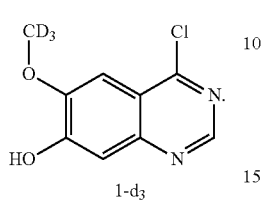
1-d₃

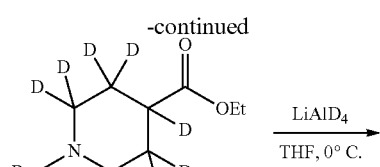

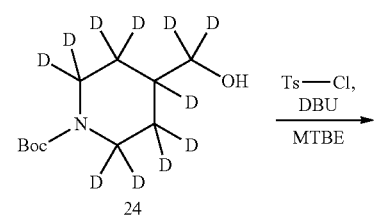

Scheme 3b. Synthesis of Piperidine 2-d₂.

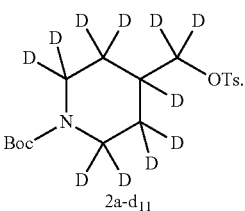

The synthesis of an appropriately deuterated quinazoline 1 is depicted in Scheme 2 above. Commercially available methyl-3,4-dihydroxybenzoate 10 is regio selectively O-alkylated with benzyl bromide to afford benzyl ether 11. Subsequent O-methylation with commercially available deuteromethyl iodide produces the d₃-methyl ether 12. Regioselective nitration of 12 and subsequent reduction of the intermediate nitrobenzene affords aniline 13. Cyclization of aniline 13 with formamidine produces quinazolinone 14. Selective deprotection of the benzyl ether of 14 with TFA-H₂O affords the 7-hydroxy-quinazolinone 15. Acetylation of 15 with Ac₂O gives the 7-acetoxy-quinazolinone 16 which is subsequently chlorinated to give the 4-chloro-quinazoline 17. Lastly, hydrolysis of the acetate of 17 with 10% NH₃/MeOH produces the appropriately deuterated quinazoline, 1-d₃.

Scheme 3a. Synthesis of Methyl Piperidines 2 and 2a-d₁₁.

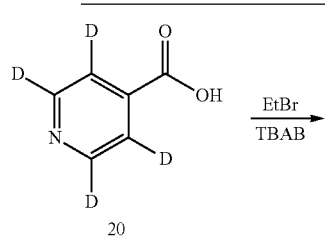

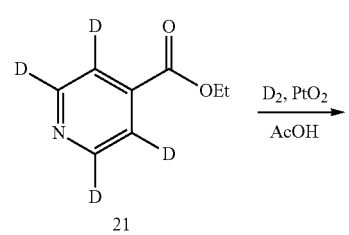

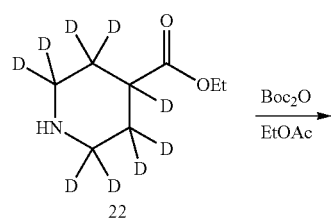

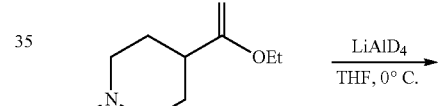

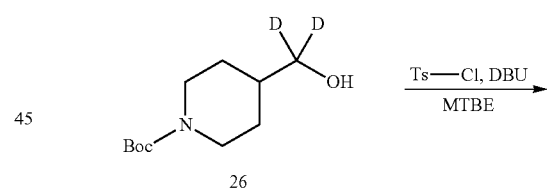

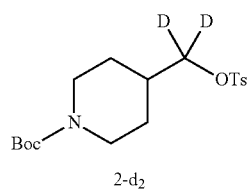
2-d₂

Scheme 3c. Synthesis of Piperidine 2.

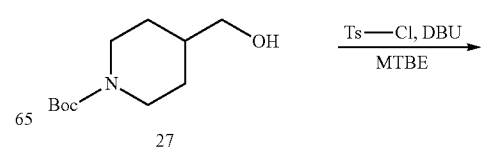
27

-continued

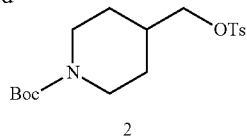

2

The synthesis of several appropriately deuterated (or undeuterated) methylpiperidines 2 and 2a is shown in Schemes 3a, 3b and 3c above. In Scheme 3a, utilizing the procedures described in G Bram et al, Heterocycles 1985, 23:875-880, commercially available isonicotinic-d4 acid 20 is treated with ethyl bromide and tetrabutylammonium bromide (TBAB) to give the corresponding ethyl ester 21. The ester 21 is then reduced with deuterium gas over $PtO_2$ using the procedure from Collins, I et al, Bioorg Med Chem Lett 2000, 10(12):1381-1384 to give piperidine 22. N-Protection of piperidine 22 is followed by reduction with lithium aluminum deuteride to give alcohol 24 which is converted to the corresponding tosylate $2\text{-}d_1"$ using the procedures described in the WO 01/32651.

In Scheme 3b, utilizing the procedures described in WO 01/32651, commercially available ethyl N-Boc-piperidine-4-carboxylate 25 is treated with lithium aluminum deuteride to afford alcohol 26 which is then treated with treated with p-toluenesulfonylchloride and DBU in MTBE to give the tosylate $2\text{-}d_2$.

In Scheme 3c, utilizing the procedures described in WO 01/32651, commercially available N-Boc-4-piperidinemethanol 27 is treated with p-toluenesulfonylchloride and DBU in MTBE to afford the undeuterated protected tosylate 2.

The specific approaches and compounds shown above are not intended to be limiting. The chemical structures in the schemes herein depict variables that are hereby defined commensurately with chemical group definitions (moieties, atoms, etc.) of the corresponding position in the compound formulae herein, whether identified by the same variable name (i.e., $R^1$, $R^2$, $R^3$, etc.) or not. The suitability of a chemical group in a compound structure for use in the synthesis of another compound is within the knowledge of one of ordinary skill in the art.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene T W et al., *Protective Groups in Organic Synthesis, 3rd Ed.*, John Wiley and Sons (1999); Fieser L et al., *Fieser and Fieser's Reagents for Organic Synthesis*, John Wiley and Sons (1994); and Paquette L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pyrogen-free compositions comprising an effective amount of a compound of Formula I or Ia (e.g., including any of the formulae herein), or a pharmaceutically acceptable salt of said compound; and an acceptable carrier. Preferably, a composition of this invention is formulated for pharmaceutical use ("a pharmaceutical composition"), wherein the carrier is a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the patient, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as Vandetanib. Such agents include those indicated as being useful in combination with Vandetanib, including but not limited to, those described in EP 1244647, WO 98/13354, WO 2006/035204, WO 2006/048633, WO 2004/032937, WO 2005/004870, WO 2004/071397, WO 2004/014426, WO 2004/014383, WO 2003/074045, WO 2003/039551, and WO 2001/074360.

In one embodiment, the second therapeutic agent is an agent useful in the treatment or prevention of a cancer.

In one embodiment, the second therapeutic agent is selected from 5-fluorouracil, folinic acid, irinotecan, docetaxel, capecitabine, oxaliplatin, bevacizumab, cyclophosphamide, methotrexate, pemetrexed, cisplatin, carboplatin, irinotecan, cetuximab, vinorelbine, gemcitabine, paclitaxel, prednisolone, 13-cis retinoic acid, erlotinib, anastrozole, leucovorin and combinations thereof.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to reduce or ameliorate the severity, duration or progression of the disorder being treated, prevent the advancement of the disorder being treated, cause the regression of the disorder being treated, or enhance or improve the prophylactic or therapeutic effect(s) of another therapy.

The interrelationship of dosages for animals and humans (based on milligrams per meter squared of body surface) is described in Freireich et al., (1966) Cancer Chemother. Rep 50: 219. Body surface area may be approximately determined from height and weight of the patient. See, e.g., Scientific Tables, Geigy Pharmaceuticals, Ardsley, N.Y., 1970, 537.

In one embodiment, an effective amount of a compound of this invention can range from 10-600 mg once daily. In another embodiment an effective amount of a compound of this invention can range from about 10-300 mg once daily.

Effective doses will also vary, as recognized by those skilled in the art, depending on the diseases treated, the severity of the disease, the route of administration, the sex, age and general health condition of the patient, excipient usage, the possibility of co-usage with other therapeutic treatments such as use of other agents and the judgment of the treating physician. For example, guidance for selecting an effective dose can be determined by reference to the prescribing information for vandetanib.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of modulating the activity of VEGFR-2/KDR tyrosine kinase in a cell, comprising contacting the cell with one or more compounds of Formula I herein.

According to another embodiment, the invention provides a method of treating a patient suffering from, or susceptible to, a disease that is beneficially treated by Vandetanib comprising the step of administering to said patient an effective amount of a compound or a composition of this invention. Such diseases are well known in the art and are disclosed in, but not limited to the following patents and published applications:
EP 1244647, WO 97/30035, WO 98/13354. Such diseases include, but are not limited to, cancer, diabetes, psoriasis, rheumatoid arthritis, Kaposi's sarcoma, hemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation.

In one particular embodiment, the method of this invention is used to treat a patient suffering from or susceptible to cancer.

In another particular embodiment, the method of this invention is used to treat a patient suffering from or susceptible to a disease or condition selected from non-small cell lung cancer, hepatocellular carcinoma, colorectal cancer, medullary thyroid cancer, breast cancer, brain tumors, solid tumors, other lung cancer, head and neck cancer, gliomas, neuroblastomas, Von Hippel-Lindau Syndrome and kidney tumors, fallopian tube cancer, ovarian cancer, peritoneal cavity cancer, transitional cell cancer, prostate cancer, cancer of the esophagus and gastroesophageal junction, and adenocarcinoma.

Methods delineated herein also include those wherein the patient is identified as in need of a particular stated treatment. Identifying a patient in need of such treatment can be in the judgment of a patient or a health care professional and can be subjective (e.g. opinion) or objective (e.g. measurable by a test or diagnostic method).

In another embodiment, any of the above methods of treatment comprises the further step of co-administering to said patient one or more second therapeutic agents. The choice of second therapeutic agent may be made from any second therapeutic agent known to be useful for co-administration with Vandetanib. The choice of second therapeutic agent is also dependent upon the particular disease or condition to be treated. Examples of second therapeutic agents that may be employed in the methods of this invention are those set forth above for use in combination compositions comprising a compound of this invention and a second therapeutic agent.

In particular, the combination therapies of this invention include co-administering a compound of Formula I or Ia and a second therapeutic agent for treatment of the following conditions (with the particular second therapeutic agent indicated in parentheses following the indication: non-small cell lung cancer (docetaxel; pemetrexed; carboplatin and paclitaxel; vinorelbine and cisplatin; gemcitabine and cisplatin; erlotinib; vandetanib), colorectal cancer (FOLFOX; FOLFIRI; capecitabine, oxaliplatin, and bevacizumab; cetuximab and irinotecan; 5-fluorouracil, leucovorin and irinotecan), breast cancer (cyclophosphamide and methotrexate; anastrozole), solid tumors (gemcitabine and capecitabine), head and neck cancer (docetaxel, cisplatin), neuroblastomas (13-cis retinoic acid), transitional cell cancer (docetaxel), prostate cancer (docetaxel and prednisolone).

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a patient does not preclude the separate administration of that same therapeutic agent, any other second therapeutic agent or any compound of this invention to said patient at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for treatment or prevention in a patient of a disease, disorder or symptom set forth above. Another aspect of the invention is a compound of Formula I for use in the treatment or prevention in a patient of a disease, disorder or symptom thereof delineated herein.

Treatment Kits

The present invention also provides kits for use to treat cancer. These kits comprise (a) a pharmaceutical composition comprising a compound of Formula I or Ia or a salt thereof, wherein said pharmaceutical composition is in a container; and (b) instructions describing a method of using the pharmaceutical composition to treat cancer.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits of this invention may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain embodiment, the kits of this invention may comprise in a separate vessel of container a pharmaceutical composition comprising a second therapeutic agent, such as one of those listed above for use for co-administration with a compound of this invention.

EXAMPLES

Example 1

Synthesis of N-(4-Bromo-2-fluorophenyl)-6-(methoxy-d3)-7-((1-methylpiperidin-4-yl)methoxy) quinazolin-4-amine (Compound 100)

Compound 100 was prepared as outlined in Scheme 4 below. Details of the synthesis are as follows.

Scheme 4. Preparation of Compound 100.
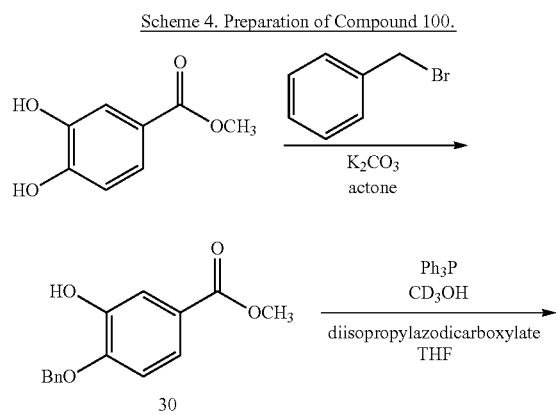
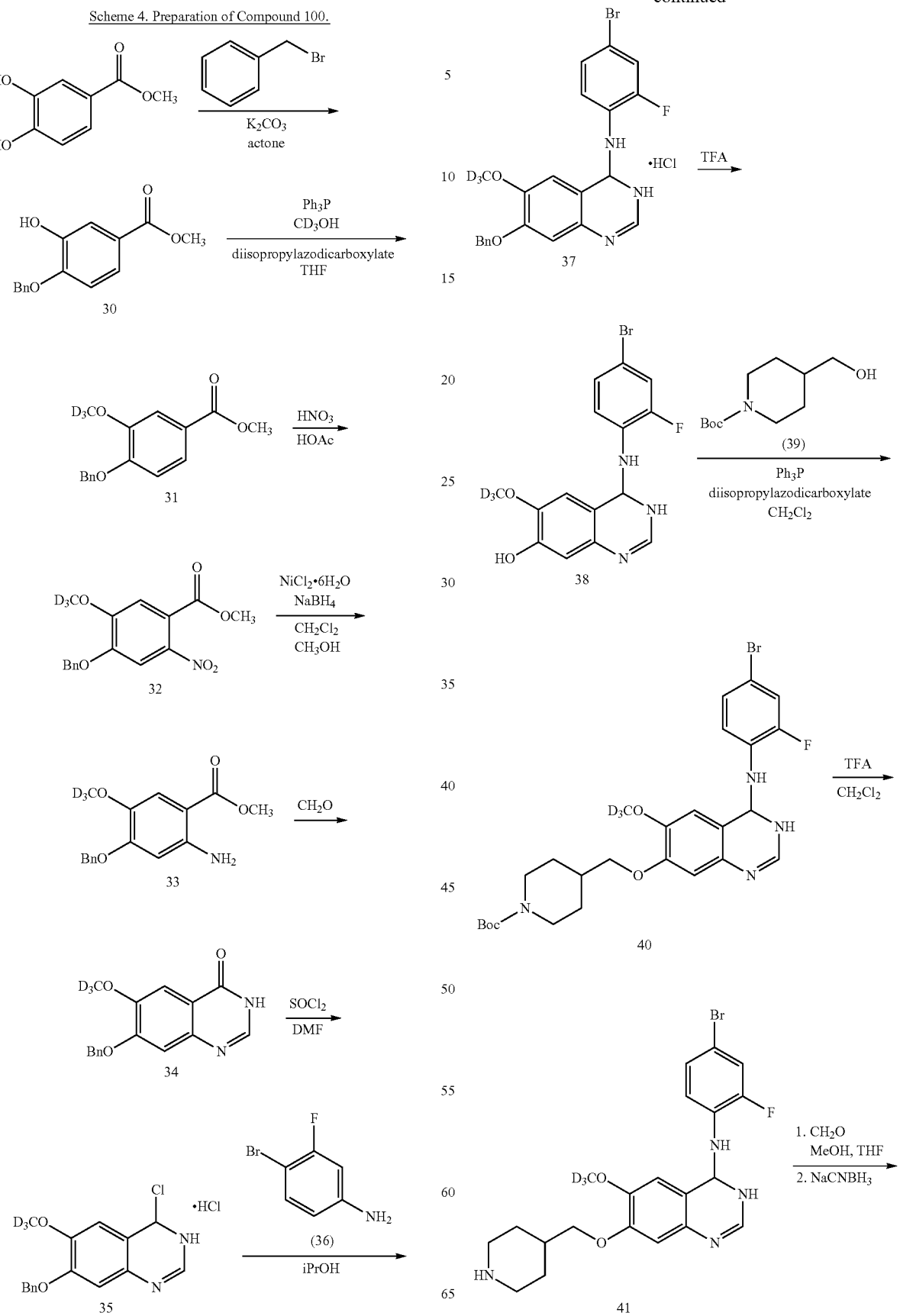

-continued

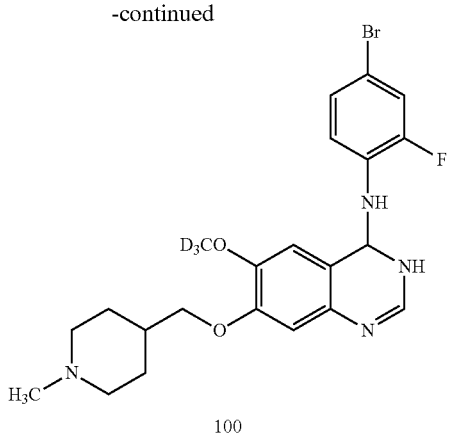

100

Synthesis of Methyl 4-(benzyloxy)-3-hydroxybenzoate (30)

To a solution of methyl 3,4-dihydroxybenzoate (10.0 g, 59.4 mmol) in acetone (400 mL) was added potassium carbonate (8.21 g, 59.5 mmol). The mixture was stirred at room temperature (rt) for 30 minutes (min). To the resulting mixture was added benzyl bromide (7 mL, 59.4 mmol) in acetone (200 mL) dropwise over 2 hours (h) and stirring was continued for 48 h. Acetone was removed under vacuum and the resulting residue was partitioned between water (100 mL) and ethyl acetate (3×25 mL). The organic layer was dried over $NaSO_4$, concentrated under vacuum and the resulting crude material purified via column chromatography to afford the product 30 (8.00 g, 52%). $^1$H NMR (300 MHz, $CDCl_3$): δ 7.70 (m, 2H), 7.50 (m, 5H), 6.95 (m, 1H), 5.70 (s, 1H), 5.10 (s, 2H), 3.93 (s, 3H). MS (M+H): 259.

Synthesis of Methyl 4-(benzyloxy)-3-(methoxy-$d_3$)benzoate (31)

To a solution of methyl 4-(benzyloxy)-3-hydroxybenzoate 30 (40 g, 146.8 mmol) in THF (600 mL) was added triphenylphosphine (46.2 g, 176.2 mmol) and methanol-$d_3$ (8.90 mL, 220 mmol). The mixture was stirred at rt under an Ar atmosphere. Diisopropyl azodicarboxylate (35.6 g, 176.2 mmol) was added dropwise and the reaction mixture was stirred for 2 h. THF was removed under reduced pressure, the residue was taken up in ethyl acetate and the mixture was washed with water. The organic layer was dried over $Na_2SO_4$ and concentrated in vacuo to afford the product 31 (40.0 g, 72%). $^1$H NMR (300 MHz, DMSO-$d_6$): δ 7.70 (m, 1H), 7.50 (m, 6H), 7.10 (m, 1H), 5.10 (s, 2H), 3.82 (s, 3H). MS (M+H): 276.

Synthesis of Methyl 4-(benzyloxy)-5-(methoxy-$d_3$)-2-nitrobenzoate (32)

A solution of methyl 4-(benzyloxy)-3-(methoxy-$d_3$)benzoate 31 (24.0 g, 87.1 mmol) in acetic acid (240 mL) was added dropwise to nitric acid (47 mL, 70%) at 0-5° C. The mixture was stirred at rt for 12 h. The resulting yellow solid was washed with ice water and filtered to afford 32 (23.0 g, 82%). MS (M+H): 321.

Synthesis of Methyl 2-amino-4-(benzyloxy)-5-(methoxy-$d_3$)benzoate (33)

To a solution of methyl 4-(benzyloxy)-5-(methoxy-$d_3$)-2-nitrobenzoate 32 (24.0 g, 75.6 mmol) in dichloromethane (400 mL) and methanol (100 mL) was added nickel (II) chloride hexahydrate (5.10 g, 21.5 mmol). Sodium borohydride (8.90 g, 236.8 mmol) was added to the reaction mixture in portions at 0-5° C. over 30 min and the mixture was stirred for 1 h. The resulting mixture was concentrated under vacuum and the residue was taken up in cold 2N HCl (500 mL). The mixture was extracted with ethyl acetate. After washing with brine and drying ($Na_2SO_4$), the organic layer was concentrated under vacuum to afford the product 33 (16.0 g, 76%). MS (M+H): 291.

Synthesis of 7-(Benzyloxy)-6-(methoxy-$d_3$)quinazolin-4(3H)-one (34)

A solution of methyl 2-amino-4-(benzyloxy)-5-(methoxy-$d_3$)benzoate 33 (15.0 g, 51.6 mmol) in formamide (110 mL) was stirred at reflux for 12 h. The resulting solid was washed with water and filtered to afford 34 (12.0 g, 81%). $^1$H NMR (300 MHz, DMSO-$d_6$): δ 12.10 (s, 1H), 7.95 (s, 1H), 7.70-7.30 (m, 2H), 7.20 (s, 1H), 5.20 (s, 2H). MS (M+H): 286.

Synthesis of 7-(Benzyloxy)-4-chloro-6-(methoxy-$d_3$) quinazoline (35)

To a solution of 7-(benzyloxy)-6-(methoxy-$d_3$)quinazolin-4(3H)-one 34 (10.0 g, 33.0 mmol) in thionyl chloride (120 mL) was added a catalytic amount of DMF. The mixture was stirred at reflux for 2 h. Thionyl chloride was removed under vacuum and the gummy residue was washed twice with toluene to afford 35 as a solid (10.0 g, 93%).

Synthesis of 7-(Benzyloxy)-N-(4-bromo-2-fluorophenyl)-6-(methoxy-$d_3$)quinazolin-4-amine hydrochloride (37)

A solution of 7-(benzyloxy)-4-chloro-6-(methoxy-$d_3$) quinazoline 35 (10.0 g, 32.9 mmol) and 4-bromo-2-fluoroaniline 36 (7.50 g, 39.4 mmol) in IPA (200 mL) was heated to 90° C. and stirred under an Ar atmosphere for 2 h. The reaction mixture was cooled to rt and the resultant precipitate was filtered through a sintered glass funnel and dried under vacuum to afford 37 (14.0 g, 93%). $^1$H NMR (300 MHz, DMSO-$d_6$): δ 11.80 (s, 1H), 8.80 (s, 1H), 8.40 (s, 1H), 7.80-7.70 (m, 1H), 7.60-7.30 (m, 8H), 5.30 (s, 2H). MS (M+H): 457.

Synthesis of 4-(4-Bromo-2-fluorophenylamino)-6-(methoxy-$d_3$)quinazolin-7-ol (38)

A solution of 7-(benzyloxy)-N-(4-bromo-2-fluorophenyl)-6-(methoxy-$d_3$)quinazolin-4-amine hydrochloride 37 (14.0 g, 28.3 mmol) in trifluoroacetic acid (130 ml) was heated to 80° C. and stirred for 3 h. The reaction mixture was then added to cold water and the resultant precipitate was filtered. The solid was dissolved in methanol, then ammonia was added to pH 9-10. The precipitate was filtered to afford the product 38 (6.00 g, 57%). MS (M+H): 367; 369 (M+3).

Synthesis of t-Butyl 4-((4-(4-bromo-2-fluorophenylamino)-6-(methoxy-$d_3$)quinazolin-7-yloxy)methyl) piperidine-1-carboxylate (40)

To a solution of 4-(4-bromo-2-fluorophenylamino)-6-(methoxy-$d_3$)quinazolin-7-ol 38 (5.00 g, 13.6 mmol) in $CH_2Cl_2$ (150 mL) was added the 39 (4.40 g, 20.4 mmol), triphenylphosphine (8.90 g, 34.0 mmol) and diisopropylazodicarboxylate (6.90 g, 34.0 mmol). The resulting mixture was stirred at rt for 2 h then was concentrated under vacuum. Crude product 40 was taken directly to the next step.

Synthesis of N-(4-bromo-2-fluorophenyl)-6-(methoxy-d$_3$)-7-(piperidin-4-ylmethoxy)quinazolin-4-amine (41)

To a solution of t-butyl 4-((4-(4-bromo-2-fluorophenylamino)-6-(methoxy-d$_3$)quinazolin-7-yloxy)methyl)piperidine-1-carboxylate 40 from the previous step in CH$_2$Cl$_2$ (40 mL) was added trifluoroacetic acid (40 mL). The mixture was stirred at rt for 4 h, then was concentrated under vacuum. The resultant brown gummy mass was taken up in water and extracted with ether to remove triphenylphosphineoxide. The aqueous layer was basified with 2N NaOH and extracted with ethyl acetate to afford the product 41 (1.70 g, 24%). MS (M+H): 464; 466 (M+3).

Synthesis of N-(4-Bromo-2-fluorophenyl)-6-(methoxy-d$_3$)-7-((1-methylpiperidin-4-yl)methoxy)quinazolin-4-amine (Compound 100)

To a solution of N-(4-bromo-2-fluorophenyl)-6-(methoxy-d$_3$)-7-(piperidin-4-ylmethoxy)quinazolin-4-amine 41 (0.20 g, 0.4 mmol) in MeOH/THF (3/3 mL) was added formaldehyde (1.3 mL, 37%). The mixture was stirred at rt for 10 min before the addition of NaBH$_3$CN (0.10 g, 0.48 mmol). The resulting mixture was stirred for 1 h, then was concentrated under vacuum. The residue was taken up in diethyl ether and the organic was washed with water. The organic layer was concentrated under vacuum and the crude product purified via column chromatography over neutral alumina to afford the product Compound 100 (0.17 g, 85%). $^1$H NMR (400 MHz, DMSO-d$_6$): δ 9.55 (s, 1H), 8.34 (s, 1H), 7.77 (s, 1H), 7.67-7.64 (m, 1H), 7.54-7.44 (m, 2H), 7.17 (s, 1H), 3.99 (d, 2H), 2.82-2.79 (m, 2H), 2.17 (s, 3H), 1.93-1.88 (m, 2H), 1.77-1.75 (m, 2H), 1.39-1.30 (m, 2H), 1.22-1.17 (m, 1H). MS (M+H): 478; 480 (M+3).

Example 2

Synthesis of N-(4-Bromo-2-fluorophenyl)-6-(methoxy-d$_3$)-7-((1-methylpiperidin-4-yl)(methoxy-d$_2$))quinazolin-4-amine (Compound 103)

Compound 103 was prepared as outlined in Scheme 5 below. Details of the synthesis are set forth below.

Scheme 5. Preparation of Compound 103.

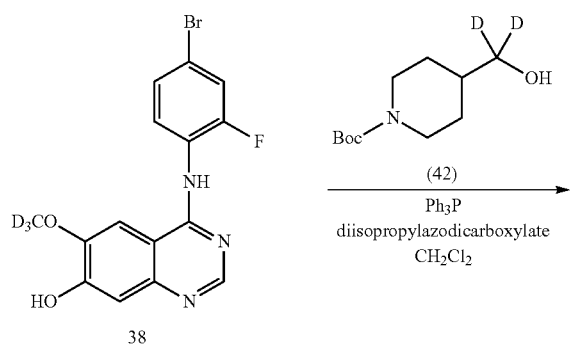

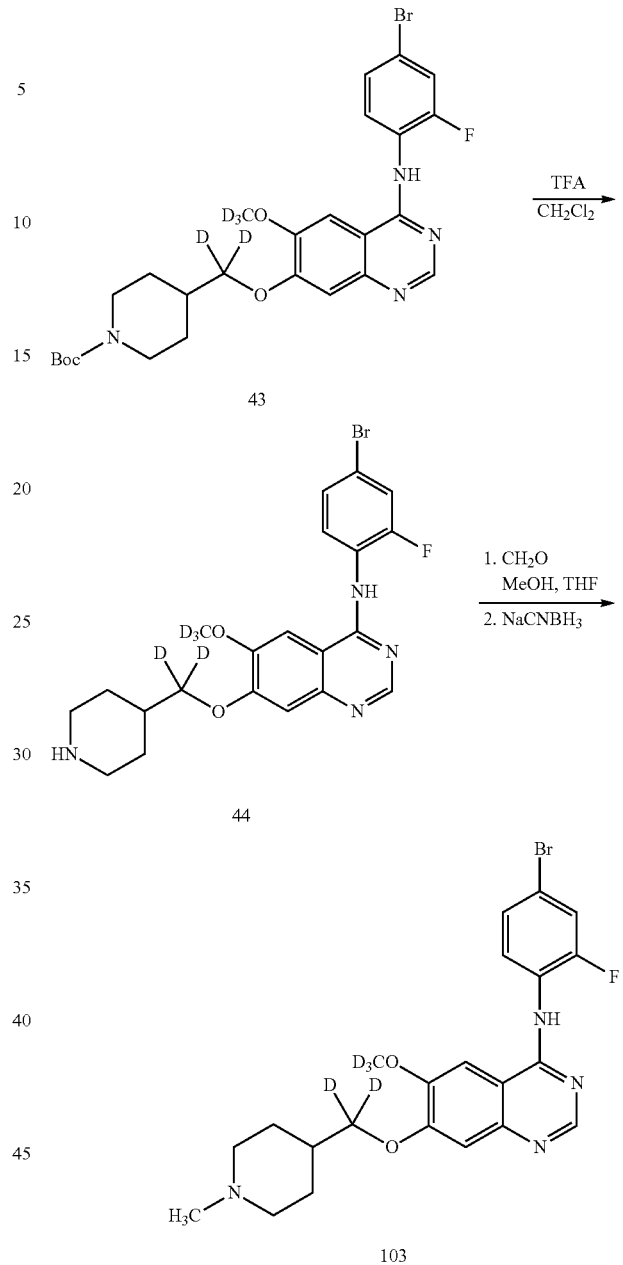

Synthesis of t-Butyl 4-((4-(4-bromo-2-fluorophenylamino)-6-(methoxy-d$_3$)-quinazolin-7-yloxy)(methyl-d$_2$))piperidine-1-carboxylate (43)

To a solution of 4-(4-bromo-2-fluorophenylamino)-6-(methoxy-d$_3$)quinazolin-7-ol 38 (4.30 g, 11.7 mmol, see Example 1) in CH$_2$Cl$_2$ (150 mL) was added the piperidine compound 42 (3.80 g, 17.5 mmol, prepared as outlined in Scheme 3b, utilizing the procedures described in WO 01/32651), triphenylphosphine (7.70 g, 29.20 mmol) and diisopropylazodicarboxylate (5.90 g, 29.2 mmol). The mixture was stirred at rt for 2 h, then was concentrated under vacuum. The crude mixture was used directly in the next step. MS (M−Boc+H): 466; 468 (M−Boc+3).

Synthesis of N-(4-Bromo-2-fluorophenyl)-6-(methoxy-d₃)-7-(piperidin-4-ylmethoxy-d₂))quinazolin-4-amine (44)

To a solution of 43 (from the previous step) in CH₂Cl₂ (40 mL) was added trifluoroacetic acid (40 mL). The mixture was stirred at rt for 4 h then was concentrated under vacuum. The resulting brown gummy mass was taken up in water and extracted with ether to remove triphenylphosphineoxide. The aqueous layer was basified with 2N NaOH and extracted with ethyl acetate to afford the product 44 (1.80 g, 24%). MS (M+H): 466, 468 (M+3).

Synthesis of N-(4-Bromo-2-fluorophenyl)-6-(methoxy-d₃)-7-((1-methylpiperidin-4-yl)(methoxy-d₂)) quinazolin-4-amine (Compound 103)

To a solution of 44 (0.20 g, 0.4 mmol) in MeOH/THF (3/3 mL) was added formaldehyde (1.3 mL, 37% in water). The mixture was stirred at rt for 10 min before the addition of NaBH₃CN (0.10 g, 0.48 mmol). The mixture was then stirred for 1 h at rt. Solvents were removed under vacuum and the residue was taken up diethyl ether. The mixture was washed with water and organic layer was concentrated under vacuum. The crude material was purified via column chromatography over neutral alumina to afford the product 103 (0.17 g, 85%). $^1$H NMR (400 MHz, DMSO-d₆): δ 9.55 (s, 1H), 8.30 (s, 1H), 7.80 (s, 1H), 7.70-7.60 (s, 1H), 7.50-7.40 (m, 2H), 7.10 (s, 1H), 2.90 (d, 2H), 2.10 (s, 3H), 1.95-1.85 (m, 2H), 1.80-1.70 (m, 2H), 1.40-1.30 (m, 2H), 1.30-1.10 (m, 1H). MS (M+H): 480.

Example 3

Synthesis of N-(4-Bromo-2-fluorophenyl)-6-(methoxy-d₃)-7-((1-(methylpiperidin-d₁₂)-4-yl)(methoxy-d₂))quinazolin-4-amine (Compound 127)

Compound 127 was prepared as outlined in Scheme 6 below. Details of the synthesis are set forth below.

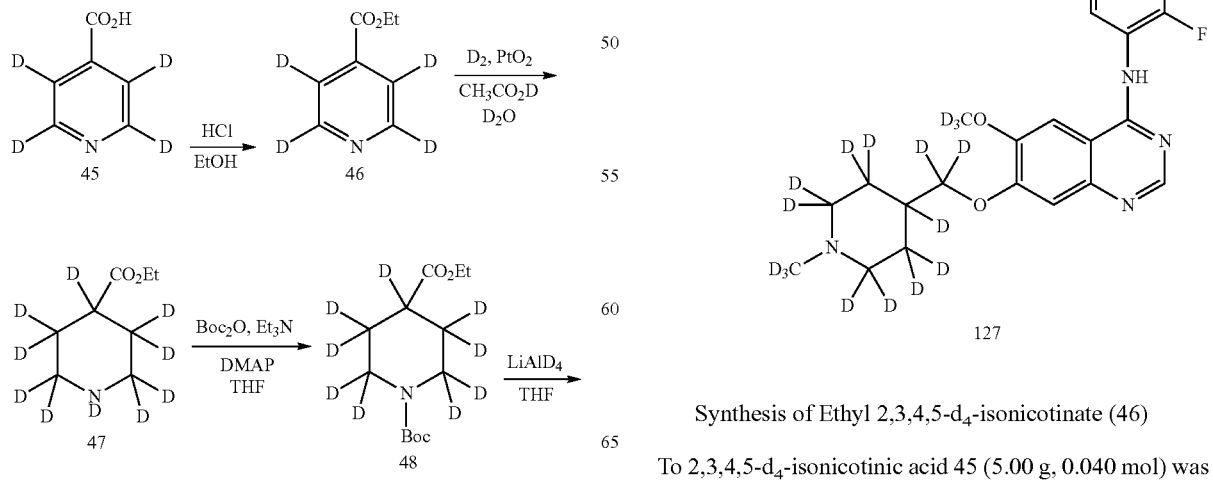

Synthesis of Ethyl 2,3,4,5-d₄-isonicotinate (46)

To 2,3,4,5-d₄-isonicotinic acid 45 (5.00 g, 0.040 mol) was added HCl in EtOH and the solution was stirred at reflux overnight. The reaction mixture was concentrated under vacuum to yield crude 46 (5.50 g, 72%) which was used directly in the next step. MS (M+H): 156.

Synthesis of Ethyl 2,2,3,3,4,5,5,6,6-d$_9$-piperidine-4-carboxylate (47)

To a solution of 46 (1.00 g, 5.21 mmol) in AcOD/D$_2$O (3 mL/9 mL) was added PtO$_2$ (0.10 g) and the mixture was subjected to deuterogenation for 48 h. The reaction mixture was filtered through Celite and the filtrate was concentrated under vacuum to give 47 as the acetic acid-d$_1$ salt (1.40 g). $^1$H NMR (400 MHz, DMSO-d$_6$): δ 4.10 (q, 2H), 1.90 (s, 3H), 1.20 (t, 2H).

Synthesis of 1-t-Butyl 4-ethyl 2,2,3,3,4,5,5,6,6-d$_9$-piperidine-1,4-dicarboxylate (48)

To a solution of the acetic acid-d$_1$ salt of 47 (1.20 g, 5.92 mmol) in THF (10 mL) was added di-t-butyl dicarbonate (1.55 g, 7.11 mmol), NEt$_3$ (1.19 g, 11.85 mmol) and DMAP (catalytic amount). The reaction mixture was stirred at rt for 2 h then was concentrated under vacuum. The residue was taken up in water and extracted with ethyl acetate (2×10 mL). The organic layer was dried over Na$_2$SO$_4$ and concentrated under vacuum to give 48 (1.20 g, 85.7%). $^1$H NMR (400 MHz, DMSO-d$_6$): δ 4.10 (q, 2H), 1.40 (s, 9H), 1.20 (t, 3H).

Synthesis of t-Butyl 4-(hydroxylmethyl-d$_2$))-2,2,3,3,4,5,5,6,6-d$_9$-piperidine-1-carboxylate (49)

To a suspension of LiAlD$_4$ (0.50 g, 11.64 mmol) in THF (30 mL) was added the ester 48 (3.10 g, 11.64 mmol) in THF (10 mL). The mixture was stirred at rt for 2 h before the addition of 10% NaOH (0.5 mL) and H$_2$O (0.5 mL). The mixture was filtered and concentrated under vacuum to give the alcohol 49 (3.00 g, 81.9%) as colorless oil. MS (M−Boc+H): 127.

Synthesis of t-Butyl 4-((4-(4-bromo-2-fluorophenylamino)-6-(methoxy-d$_3$)quinazolin-7-yloxy)(methyl-d$_2$))-2,2,3,3,4,5,5,6,6-d$_9$-piperidine-1-carboxylate (50)

To a solution of 38 (4.30 g, 11.7 mmol, see Example 1) in CH$_2$Cl$_2$ (150 mL) was added the 49 (3.80 g, 17.5 mmol), triphenylphosphine (7.70 g, 29.20 mmol) and diisopropylazodicarboxylate (5.90 g, 29.2 mmol). The mixture was stirred at rt for 2 h. CH$_2$Cl$_2$ was removed under vacuum and the crude 50 was used directly in the next step. MS (M−Boc+H): 475; 477 (M−Boc+3).

Synthesis of N-(4-bromo-2-fluorophenyl)-6-(methoxy-d$_3$)-7-(2,2,3,3,4,5,5,6,6-d$_9$-piperidin-4-yl-methoxy-d$_2$))quinazolin-4-amine (51)

To a solution of 50 (7.50 g) from the previous step in CH$_2$Cl$_2$ (25 mL) was added trifluoroacetic acid (25 mL). The reaction mixture was stirred at rt for 4 h, then was concentrated under vacuum to a brown gummy mass. The crude residue was taken up in water and extracted with ether to remove triphenylphosphineoxide. The aqueous layer was basified with 2N NaOH and extracted with ethyl acetate to afford the product 51 (0.90 g, 24%). MS (M+H): 475; 477 (M+3).

Synthesis of N-(4-bromo-2-fluorophenyl)-6-(methoxy-d$_3$)-7-((1-(methyl-d$_3$)-2,2,3,3,4,5,5,6,6-d$_9$-piperidin-4-yl)(methoxy-d$_2$))quinazolin-4-amine (127)

To a solution of 51 (0.90 g, 1.9 mmol) in MeOD/THF (5/5 mL) was added formaldehyde-d$_2$ (0.17 mg, 37% in D$_2$O, 5.7 mmol). The mixture was stirred at rt for 10 min followed by the addition of NaBD$_3$CN (0.14 g, 2.28 mmol). The mixture was stirred for 1 h, then was concentrated under vacuum. The residue was taken up in diethyl ether and washed with water. The organic layer was concentrated under vacuum and the resulting crude material was purified via column chromatography over neutral alumina to afford the product 127 (0.11 g, 12%). $^1$H NMR (400 MHz, DMSO-d$_6$): δ 9.55 (s, 1H), 8.30 (s, 1H), 7.80 (s, 1H), 7.70-7.60 (m, 1H), 7.50-7.40 (m, 2H), 7.10 (s, 1H). MS (M+H): 492; 494 (M+3).

Evaluation of Metabolic Stability

Certain in vitro liver metabolism studies have been described previously in the following references, each of which is incorporated herein in their entirety: Obach, R S, Drug Metab Disp, 1999, 27:1350; Houston, J B et al., Drug Metab Rev, 1997, 29:891; Houston, J B, Biochem Pharmacol, 1994, 47:1469; Iwatsubo, T et al., Pharmacol Ther, 1997, 73:147; and Lave, T, et al., Pharm Res, 1997, 14:152.

Microsomal Assay:

Human liver microsomes (20 mg/mL) are obtained from Xenotech, LLC (Lenexa, Kans.). β-nicotinamide adenine dinucleotide phosphate, reduced form (NADPH), magnesium chloride (MgCl$_2$), and dimethyl sulfoxide (DMSO) are purchased from Sigma-Aldrich. The incubation mixtures are prepared according to Table 2:

TABLE 2

| Reaction Mixture Composition for Human Liver Microsome Study | |
|---|---|
| Liver Microsomes | 3.0 mg/mL |
| Potassium Phosphate, pH 7.4 | 100 mM |
| Magnesium Chloride | 10 mM |

Determination of Metabolic Stability:

Two aliquots of this reaction mixture are used for a compound of this invention. The aliquots are incubated in a shaking water bath at 37° C. for 3 minutes. The test compound is then added into each aliquot at a final concentration of 0.5 µM. The reaction is initiated by the addition of cofactor (NADPH) into one aliquot (the other aliquot lacking NADPH serves as the negative control). Both aliquots are then incubated in a shaking water bath at 37° C. Fifty microliters (50 µL) of the incubation mixtures are withdrawn in triplicate from each aliquot at 0, 5, 10, 20, and 30 minutes and combined with 50 µL of ice-cold acetonitrile to terminate the reaction. The same procedure is followed for vandetanib and the positive control, 7-ethoxycoumarin. Testing is done in triplicate.

Data Analysis:

The in vitro $t_{1/2}$s for test compounds are calculated from the slopes of the linear regression of % parent remaining (ln) vs incubation time relationship.

in vitro $t_{1/2} = 0.693/k$ k=−[slope of linear regression of % parent remaining (ln) vs incubation time]

Data analysis is performed using Microsoft Excel Software.

The metabolic stability of compounds of Formula I or Ia is tested using pooled liver microsomal incubations. Full scan LC-MS analysis is then performed to detect major metabolites. Samples of the test compounds, exposed to pooled human liver microsomes, are analyzed using HPLC-MS (or MS/MS) detection. For determining metabolic stability, multiple reaction monitoring (MRM) is used to measure the disappearance of the test compounds. For metabolite detection, Q1 full scans are used as survey scans to detect the major metabolites.

SUPERSOMES™ Assay.

Various human cytochrome P450-specific SUPERSOMES™ are purchased from Gentest (Woburn, Mass., USA). A 1.0 mL reaction mixture containing 25 pmole of SUPERSOMES™, 2.0 mM NADPH, 3.0 mM MgCl, and 1 μM of a compound of Formula I in 100 mM potassium phosphate buffer (pH 7.4) is incubated at 37° C. in triplicate. Positive controls contain 1 μM of vandetanib instead of a compound of Formula I. Negative controls use Control Insect Cell Cytosol (insect cell microsomes that lack any human metabolic enzyme) purchased from GenTest (Woburn, Mass., USA). Aliquots (50 μL) are removed from each sample and placed in wells of a multi-well plate at various time points (e.g., 0, 2, 5, 7, 12, 20, and 30 minutes) and to each aliquot is added 50 μL of ice cold acetonitrile with 3 μM haloperidol as an internal standard to stop the reaction.

Plates containing the removed aliquots are placed in −20° C. freezer for 15 minutes to cool. After cooling, 100 μL of deionized water is added to all wells in the plate. Plates are then spun in the centrifuge for 10 minutes at 3000 rpm. A portion of the supernatant (100 μL) is then removed, placed in a new plate and analyzed using Mass Spectrometry.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

I claim:

1. A compound of Formula I

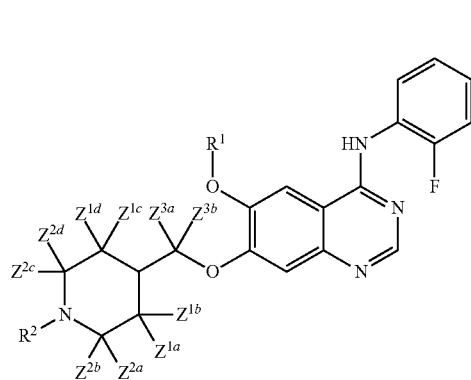

(I)

or a pharmaceutical salt thereof; wherein:
each Z is independently selected from hydrogen or deuterium;
each R is selected from —$CH_3$, —$CH_2D$, —$CHD_2$ and $CD_3$; and
when each R is —$CH_3$ at least one Z is deuterium,
wherein there is at least 50.1% incorporation of deuterium at any atom designated as D or deuterium.

2. A compound of Formula A

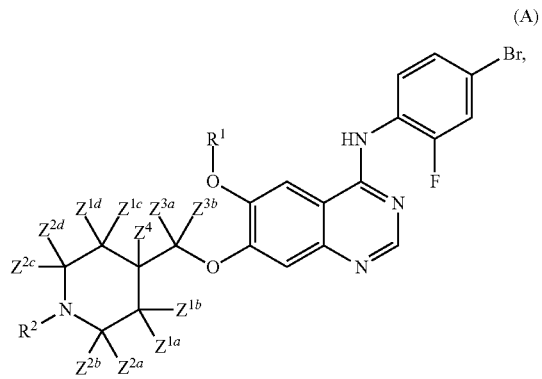

(A)

or a pharmaceutically acceptable salt thereof; wherein:
each Z is independently selected from hydrogen and deuterium;
each R is selected from —$CH_3$, —$CH_2D$, —$CHD_2$ and $CD_3$; and
when each R is —$CH_3$ at least one Z is deuterium,
wherein there is at least 50.1% incorporation of deuterium at any atom designated as D or deuterium.

3. The compound of claim 2, wherein each $Z^1$ is the same.
4. The compound of claim 3, wherein each $Z^2$ is the same.
5. The compound of claim 4, wherein each $Z^3$ is the same.
6. The compound of claim 5, wherein $R^1$ is selected from $CH_3$ and $CD_3$.
7. The compound of claim 6, wherein $R^2$ is selected from $CH_3$ and $CD_3$.
8. The compound of claim 7 wherein $Z^4$ is hydrogen.
9. The compound of claim 8, selected from any one of the compounds set forth in the table:

| Cmpd | $R^1$ | $R^2$ | Each $Z^3$ | Each $Z^1$ | Each $Z^2$ |
|---|---|---|---|---|---|
| 100 | $CD_3$ | $CH_3$ | H | H | H |
| 101 | $CH_3$ | $CD_3$ | H | H | H |
| 102 | $CH_3$ | $CH_3$ | D | H | H |
| 103 | $CD_3$ | $CH_3$ | D | H | H |
| 104 | $CH_3$ | $CD_3$ | D | H | H |
| 105 | $CD_3$ | $CD_3$ | H | H | H |
| 106 | $CD_3$ | $CD_3$ | D | H | H |
| 107 | $CD_3$ | $CH_3$ | H | D | H |
| 108 | $CH_3$ | $CD_3$ | H | D | H |
| 109 | $CH_3$ | $CH_3$ | D | D | H |
| 110 | $CD_3$ | $CH_3$ | D | D | H |
| 111 | $CH_3$ | $CD_3$ | D | D | H |
| 112 | $CD_3$ | $CD_3$ | H | D | H |
| 113 | $CD_3$ | $CD_3$ | D | D | H |
| 114 | $CD_3$ | $CH_3$ | H | H | D |
| 115 | $CH_3$ | $CD_3$ | H | H | D |
| 116 | $CH_3$ | $CH_3$ | D | H | D |
| 117 | $CD_3$ | $CH_3$ | D | H | D |
| 118 | $CH_3$ | $CD_3$ | D | H | D |
| 118 | $CD_3$ | $CD_3$ | H | H | D |
| 119 | $CD_3$ | $CD_3$ | D | H | D |
| 120 | $CD_3$ | $CH_3$ | H | D | D |
| 121 | $CH_3$ | $CD_3$ | H | D | D |
| 122 | $CH_3$ | $CH_3$ | D | D | D |
| 123 | $CD_3$ | $CH_3$ | D | D | D |
| 124 | $CH_3$ | $CD_3$ | D | D | D |
| 125 | $CD_3$ | $CD_3$ | H | D | D |
| 126 | $CD_3$ | $CD_3$ | D | D | D. |

10. The compound of claim 7 wherein $Z^4$ is deuterium.

11. The compound of claim 10 which is

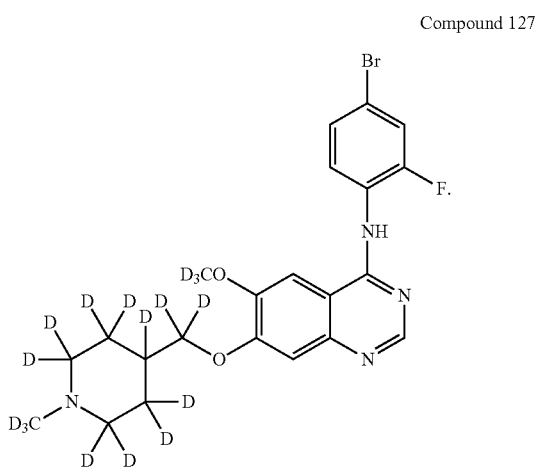

Compound 127

12. The compound of claim 1, wherein any atom not designated as deuterium is present at its natural isotopic abundance.

13. A pyrogen-free pharmaceutical composition comprising a compound of claim 2; and a pharmaceutically acceptable carrier.

14. The composition of claim 13 further comprising a second anti-cancer agent.

15. The composition of claim 14, wherein the second anti-cancer agent is selected from one or more of 5-fluorouracil, folinic acid, irinotecan, docetaxel, capecitabine, oxaliplatin, bevacizumab, cyclophosphamide, methotrexate, pemetrexed, cisplatin, carboplatin, irinotecan, cetuximab, vinorelbine, gemcitabine, paclitaxel, prednisolone, 13-cis retinoic acid, erlotinib, anastrozole, and leucovorin.

16. A method of inhibiting the activity of VEGFR-2/KDR tyrosine kinase in a cell, comprising the step of contacting the cell with a compound of claim 2.

17. A method of treating a patient suffering from thyroid cancer, comprising the step of administering to the patient in need thereof a composition of claim 13.

* * * * *